US006197756B1

(12) United States Patent
Zoldhelyi et al.

(10) Patent No.: US 6,197,756 B1
(45) Date of Patent: Mar. 6, 2001

(54) GENE TRANSFER OF E2F-1 TO INHIBIT VASCULAR SMOOTH MUSCLE CELL ACCUMULATION IN VASCULAR TISSUE

(75) Inventors: Pierre Zoldhelyi, Bellaire; James T. Willerson, Houston, both of TX (US)

(73) Assignee: Texas Heart Institute, Houston, TX (US)

(*) Notice: Subject to any disclaimer, the term of this patent is extended or adjusted under 35 U.S.C. 154(b) by 0 days.

(21) Appl. No.: 09/416,929

(22) Filed: Oct. 13, 1999

Related U.S. Application Data (60) Provisional application No. 60/104,801, filed on Oct. 19, 1998.

(51) Int. Cl.[7] .............................. A61K 31/70; C12Q 1/68; C12P 21/06
(52) U.S. Cl. ................ 514/44; 435/6; 435/69.1
(58) Field of Search .............................. 514/44; 536/23.1; 435/320.1, 325, 455, 70.1; 800/8; 424/93.1

(56) References Cited

PUBLICATIONS

Bennett et al. Circulation Research 82:704–712, Apr. 1998.*
Claudio et al. Circulation Research 851032–1039, Nov. 1999.*
Kaneda et al. Annals New York Academy of Sciences 811:299–310, Apr. 1997.*
Lee et al. Antisense & nucleic acid drug development 9:487–492, Oct. 1999.*
Mann Antisense& nucleic acid drug development 8:171–176, Apr. 1998.*
Mann et al. The Lancet 354:1493–1498, Oct. 1999.*
Morishita et al. PNAS 92:5855–5459, Jun. 1995.*
Smith et al. Circulation 96:1899–1905, Sep. 1997.*
Spyridopoulos et al. Circulation 98:2883–2890, Dec. 1998.*
Thibault et al. Molecular Medicine 3(8):519–529, Aug. 1997.*
Zoldhelyi et al. Seminars in intervention cardiology 4:151–165, Sep. 1999.*
Kirshenbaum et al; Human E2F–1 Reactivates Cell Cycle Progression in Ventricular Myocytes and Represses Cardiac Gene Transcription, Developmental Biology; Nov. 1, 1996; vol. 179, No. 2; pp. 402–411.
Helin et al; Abstract: A cDNA Encoding a pRB–Binding Protein with Properties of the Transcription factor E2F; Database Medline on STN, US National Library of Medicine (Bethesda, MD); No. 92346720; Cell, Jul. 24, 1992.
Zoldhelyi, et al; Adenovirus–mediated Gene Transfer of Recombinant Tissue Factor Pathway Inhibitor in Vitro and in Vivo Journal of the American College of Cardiology; Feb. 1998; vol. 31, Issue 21001, Supplement 1, p. 145A; abstract No. 1063–108.
Bennett et al; Apoptosis of Vascular Smooth Muscle Cells in Atherosclerosos; Atherosclerosis, May 1998; vol. 138, No. 1; pp. 3–9.

* cited by examiner

*Primary Examiner*—Karen M. Hauda
*Assistant Examiner*—Joseph T. Woitach
(74) *Attorney, Agent, or Firm*—McDaniel & Associates, P.C.; C. Steven McDaniel (57) ABSTRACT

Methods for induction of E2F-1 related vascular smooth muscle cell (VSMC) death to limit vascular stenosis or restenosis, to regress atherosclerotic plaque and to prevent atherogenesis are disclosed. Also disclosed is an adenovirus vector containing the E2F-1 gene, and a method of transferring the gene to a vessel or graft. A method of limiting cell proliferation and/or reducing cell numbers includes transferring the E2F-1 gene into VSMC to achieve overexpression of E2F-1 gene product, which drives vascular cells into S-phase and thereby causes their subsequent death.

23 Claims, 6 Drawing Sheets

SEQUENCE LISTING

<160> NUMBER OF SEQ ID NOS: 2

<210> SEQ ID NO 1
<211> LENGTH: 19
<212> TYPE: DNA
<213> ORGANISM: Homo sapiens

<400> SEQUENCE: 1
cgtgagcgtc atggccttg                                                                                19

<210> SEQ ID NO 2
<211> LENGTH: 21
<212> TYPE: DNA
<213> ORGANISM: Homo sapiens

<400> SEQUENCE: 2
ccaagccctg tcagaaatcc a                                                                              21

GENE TRANSFER OF E2F-1 TO INHIBIT VASCULAR SMOOTH MUSCLE CELL ACCUMULATION IN VASCULAR TISSUE

CROSS REFERENCE TO PROVISIONAL APPLICATION

This application claims the benefit of U.S. Provisional application Ser. No. 60/104,801 filed Oct. 19, 1998.

FIELD OF THE INVENTION

The present disclosure concerns the field of gene therapy applied to vascular smooth muscle cells (VSMC) for the purpose of preventing formation of atherosclerotic lesions, and for treating atherosclerotic plaque and sites of vascular injury.

BACKGROUND OF THE DISCLOSURE

Vascular smooth muscle cell proliferation in response to injury is an important etiologic factor in vascular proliferative disorders such as atherosclerosis and restenosis after vascular injury caused by invasive medical techniques. Vascular injury caused by the percutaneous revascularization and other interventions stimulates the proliferation and migration of VSMC (Clowes et al., 1983, Schwartz et al., 1993, and Gordon et al., 1990). Migration of VSMC to the lumen of the injured site has been shown to be more critical to the pathogenesis of restenosis in some animal models than proliferation of VSMC per se (Schwartz et al., 1995, Schwartz et al., 1996).

This intimal accumulation of VSMC, through proliferation and migration from the media of the vessel, significantly contributes to restenosis after percutaneous revascularization interventions (Clowes et al., 1983, Schwartz et al., 1993, and Schwartz et al., 1995). The accumulation of intimal smooth muscle cell is also prominent after carotid balloon injury in rats (Clowes et al., 1983), after coronary balloon angioplasty in pigs (Schwartz et al., 1993) and in instances of restenosis after arterial dilatation in humans (Gordon et al., 1990, O'Brien et al., 1993). VSMC also contribute to the production of extracellular matrix, which increases the bulk of the neointimal mass obstructing the vessel lumen after balloon angioplasty, stenting, or other interventions that have transiently restored blood flow (Clowes et al., 1983, Schwartz et al., 1993, Schwartz et al., 1995, and Schwartz 1996).

One strategy employed for maintaining vascular patentcy after vascular injury is to induce apoptosis (cell death) of VSMC as a result of gene transfer. For example, the transfer of a replication-defective adenovirus encoding a non-phosphorylatable, constitutively active form of the retinoblastoma gene product (pRb) into VSMC inhibits the cells entry into S-phase after endovascular balloon angioplasty in rat carotid and porcine femoral artery models of restenosis (Chang et al., 1995). Adenoviral vectors encoding the herpes virus thymidine kinase (tk) gene have been introduced into porcine arteries injured with a balloon catheter (Ohno et al., 1995). When the tk gene was activated by ganciclovir treatment, intimal hyperplasia decreased.

Walsh et al. reported the prevention of restenosis with the transfer of the Fas-ligand (FasL) gene into balloon catheter injured rat carotid arteries (Sata et al., 1998). When the FasL binds to Fas (CD95) a transduction of a cytolytic signal occurs in the cell, which leads to apoptosis (Griffith, T. S. et al., 1995). Another report by Pollman and associates describes regression of vascular lesions by induction of cell death through inhibition of the death repressor gene, bcl-2 (Pollman et al., 1998). Yonemitsu et al., have described the gene transfer of p53, which was reported to prevent restenosis in balloon catheter injured rat carotid arteries (Yonemitsu et al., 1998). However, p53 induced growth arrest also occurs via the induction of p21 and, thus the p53, is not a pure "killer" gene.

The E2F-1 family of transcription factors appears to play a critical role in the transcription of certain genes required for cell cycle progression from $G_1$ to S phase. E2F-1, the first cloned member of this family, is regulated during the cell cycle at the mRNA level by changes in transcription of the E2F-1 gene and at the protein level by complex formation with proteins such as the retinoblastoma gene product (pRb), cyclin A, and DP1. The E2F-1 gene encodes a nuclear protein, retinoblastoma-associated protein 1 ("E2F-1" or "RBAP-1"), that binds to the underphosphorylated form of human retinoblastoma (pRB), a protein that is known to repress the progression of cells towards S phase.

pRb has two known major functions. One of its functions is to sequester or inactivate the transcription factor E2F-1 which is required for activation of S phase genes. The second major function is to regulate the activity of polymerase I and III (pol I and pol III). The pRB appears to be the major player in a regulatory circuit in the late $G_1$ phase, the so called restriction point. Moreover, pRb is involved in regulating an elusive switch point between cell cycle, differentiation and apoptosis.

A prerequisite for the growth-suppressing function of pRB is binding to the E2F-1 transcription factor, thus inhibiting transcriptional activation of genes by the E2F-1 protein which are required for DNA synthesis (Helin et al., 1992 and Nevins 1992) and cell cycle progression from G1 to S phase. Inactivation of pRb by either phosphorylation, mutation or oncoprotein binding disrupts the Rb/E2F complex and results in E2F-1 activation. Analogous, overexpression of E2F-1 can override the pRb-mediated Glarrest (Zhu et al., 1993, Qin et al., 1995, Neuman et al., 1996) and lead to either cellular transformation (Singh et al., 1994, Xu et al., 1995, Johnson et al., 1994b) or promote premature S phase entry (Qin et al., 1994 Shan and Lee 1994, Shan et al., 1996, Kowalik et al., 1995).

Several laboratories have shown a direct relationship in the transfer of the E2F-1 gene into cancer and immortalized cells and the subsequent apoptotic death of those cells. An adenovirus carrying E2F-1 (Ad.E2F-1) has been described by DeGregori et al., who observed a promotion of quiescent transformed immortalized rat fibroblast cell line, REF52, into S-phase and apoptosis (cell death), after E2F-1 gene transfer (DeGregori et al., 1997). Hunt et al., have shown that Ad.E2F-1 can kill in vitro human breast and ovarian carcinoma cell lines (Hunt et al., 1997). The E2F-1 gene, transferred by Ad.E2F-1, induces apoptosis in tumors (gliomas) in vivo, resulting in the regression of tumors, thus showing the potential therapeutic promise of E2F-1 gene transfer in cancer (Fueyo et al., 1998). Agah and associates transferred the E2F-1 gene into adult rat ventricular myocytes both in vivo and in vitro in an effort to induce myocyte proliferation after infarction (Agah et al., 1997). Instead they found that E2F-1 gene transfer led to apoptosis of the myocytes independent of the tumor suppressor protein p53.

Other reports suggested that overexpression of E2F-1 was associated with accelerated proliferation of cultured fibroblasts (Johnson et al., 1994). E2F-1 appears to have divergent growth regulatory functions, dependent on tissue type, developmental stage, and the coexistence of other genes.

Prior to the present invention, no previous investigation of E2F-1 gene transfer to non-tumoral or non-immortal cell lines or tissue had been performed.

Prior to the invention herein, it was not known whether the migration and proliferation of normal vascular smooth muscle cells could be effectively reduced at the site of vascular injury by the local in vivo transformation of VSMC following injury. Moreover, it was not known whether gene therapy of VSMC could reduce atheroma formation in atherosclerotic disease states.

SUMMARY OF THE INVENTION

The present disclosure provides that vascular smooth muscle cells (VSMC) are driven into S-phase and thereby to their subsequent death because of E2F-1 transfer. E2F-1 transformed VSMC suppress VSMC growth, restenosis, and promotes the regression of atherosclerotic plaques. E2F-1 gene transfer to arteries and vein grafts, in accordance with methods of the disclosure, is useful to prevent atherogenesis and fibroproliferative disorders in arteries, vein grafts, arteriovenous fistulas and stent grafts.

The disclosure teaches a method of using vascular E2F-1 gene transfer to prevent vascular smooth muscle cell (VSMC) accumulation contributing to arterial restenosis after percutaneous revascularization interventions is provided. Examples of such interventions are balloon angioplasty and vascular stenting.

The present disclosure also provides a method of employing gene transfer of E2F-1 to prevent VSMC accumulation and restenosis in venous grafts, such as saphenous coronary bypass and peripheral arterial by-pass grafts.

Also provided by the present disclosure is a method of preventing VSMC accumulation and stenosis in arteriovenous fistulas used for dialysis access by transferring the E2F-1 gene.

Another method provided by the disclosure is the E2F-1 transfer to arteries and veins to reduce the primary formation of primary sclerotic lesions.

The foregoing has outlined rather broadly the features and advantages of the present invention in order that the detailed description of the invention that follows may be better understood. Additional features and advantages of the invention will be described hereinafter which form the subject of the claims of the invention.

BRIEF DESCRIPTION OF THE DRAWINGS

The novel features which are believed to be characteristic of the invention will be better understood from the following detailed description, in conjunction with the accompanying drawings.

FIG. 1. A & B: Transduction of E2F-1 into human vascular smooth muscle cells (VSMC). Human VSMC were infected for six hours with a mock control, Ad.RR and Ad.E2F-1 at a multiplicity of infection (MOI) of 50 and were immunostained for E2F-1. An example of VSMC stained 10 hours after infection with E2F-1 is shown in (panel A), whereas no immunoreactivity to E2F-1 was seen in Ad.RR infected cells harvested at the same time (panel B). Magnification 400×.

FIG. 3. A, B & C: S-Phase Entry of E2F-1 Transduced Coronary VSMC is Associated with Induction of Apoptosis. Shown are human coronary VSMC 36 hours after treatment with mock control (panel A); the null adenoviral vector, Ad.RR (panel B), and Ad.E2F-1 (panel C). Viral vectors were used at MOI 100; magnification 100×.

FIG. 5. A & B: Dose Response and Time Course of Apoptosis in VSMC Infected with Ad.E2F-1. The VSMC were infected for six hours with Ad.E2F-1, Ad.RR or mock control at MOI 10–200 followed by growth stimulation in 10% FBS. VSMC were harvested every 24 hours and subjected to DNA flow cytometry. Panel A shows the flow cytometry profile of individual treatment groups subjected to different dosages of viral vectors. Panel B indicates the percentage of cells undergoing apoptosis, as reflected by hypodiploid, cleaved DNA after Ad.E2F-1 infection.

DETAILED DESCRIPTION OF THE PREFERRED EMBODIMENTS

Vascular restenosis, a major unresolved problem for percutaneous coronary revascularization procedures, has thus far been resistant to all therapeutic strategies. The present disclosure describes a treatment strategy for restenosis which is directed toward interference with a specific cellular event that leads to neointimal formation, with a specific goal of decreasing the neointimal volume through apoptosis of proliferating VSMC.

The present invention reduces the number of VSMC at the site of vascular injury by inducing their coordinated death through E2F-1-induced apoptosis. This coordinated death of VSMC at the site of injury reduces neointimal formation by decreasing the number of VSMC available to migrate towards the lumen, to produce growth factors, and to produce extracellular matrix (Ohno et al., 1995, Chang et al., 1995). In contrast to the cell cycle arrest genes that limit VSMC growth by preventing entry of the cells into S-phase (Ohno et al., 1995, Chang et al., 1995), E2F-1 gene transfer drives the VSMC from G1 into S-phase, ultimately resulting in the apoptotic programmed death of the transformed VSMC.

Cloning and sequencing of the human E2F-1 cDNA

Extraction of mRNA from ML-1 cells was performed using the QIAGEN mRNA isolation kit (QIAGEN, Valencia, Calif.). First-strand cDNA was synthesized using superscript II RNase H-reverse transcriptase (Gibco BRL, Gaithersburg, Md.). E2F-1 sequences were prepared by polymerase chain reaction using rTth DNA polymerase XL (Perkin-Elmer,) along with the following primers:

Sequence 1
5'E2F1_sense: 5'-CGTGAGCGTCATGGCCTTTG-3' sense primer, SEQ ID NO: 1

Sequence 2
3'E2F1_antisense: 5'-CCAAGCCCTGTCAGAAATCCA-3' antisense primer, SEQ ID NO: 2 (primers were designed according to the E2F-1 sequence obtained from gene bank accession number M96577).

The polymerase chain reaction amplified fragment was cloned into pCR-Script vector, and positive clones were identified and sequenced. Double-stranded DNA sequencing was performed in the University of Texas Medical School Sequencing Core facility.

Recombinant adenovirus construction

The recombinant E2F-1 adenovirus (Ad.E2F-1) contains the human cytomegalovirus promoter, E2F-1 cDNA, and bovine growth hormone polyadenylation signal in a minigene cassette inserted into the E1-deleted region of modified adenovirus type 5 (Ad5). Replication-defective adenovirus carrying the human E2F-1 gene (Ad.E2F-1) was generated by cotransfecting the pXCJL-1 and pJM 17 plasmids, which were provided by Dr. F. L. Graham (Microbix Biosystems, Hamilton, Ontario), into 293 cells (McGrory et al., 1988). Viral stocks were propagated in 293 cells. Replication-defective adenovirus containing no foreign gene (Ad.RR) was a gift by Dr. Robert D. Gerard (Leuven, Belgium). Recombinant adenoviruses (Ad.E2F-1 and Ad.RR) were plaque-purified and purity of Ad.E2F-1 was established by immunoblotting for E2F-1 on VSMC infected with virions amplified from individual plaques. High titer adenovirus was purified from 293 cells with modification of a previously described procedure (Gomez-Foix et al., 1992). These modifications included a 30-min digestion of precipitated virions with benzonase (100 U/ml, American International Chemical, Inc., Natick, Mass.) and the addition of 2 sequential CsCl (density 1.34 mg/ml) equilibrium centrifugation steps at 180,000×g for 6 hours at 4° C. Purified recombinant virions were suspended in sucrose (2% w/vol) and $MgCl_2$ (2 mM) in PBS, desalted by sepharose CL4B exclusion chromatography (Pharmacia Corporation, Piscataway, N.J.), supplemented with 5% glycerol and stored at −80° C.

The concentration of infectious viral particles was determined in 293 cells by plaque assay as described in McGrory et al., 1988. All viral preparations were tested for endotoxin using a Limulus amebocyte lysate assay and were found to be endotoxin-free (<0.125 EU/ml).

Cell Culture

Human vascular smooth muscle cells (VSMC) were obtained for these studies from Dr. Timothy Scott-Burden (Texas Heart Institute). Passage 2 human coronary VSMC were purchased from Cascade Biologics, Inc. (Portland, Oreg.). Cells were grown in Dulbecco's modified Eagle's medium (DMEM) from Gibco or in Medium 231 from Cascade Biologics, Inc. For cell growth experiments, VSMC were seeded in triplicates at a density of approximately $10 \times 10^3/cm^2$ and were growth arrested for 60 hours in DMEM supplemented with 0.1% bovine serum albumin or in Medium 231. For infection of the VSMC, recombinant adenovirus was suspended in the growth arrest medium (DMEM with 0.1% bovine serum albumin or Medium 231). Cells were then infected for six hours with either the replication-deficient adenovirus encoding the human E2F-1 gene (Ad.E2F-1), with a recombinant adenovirus carrying the identical CMV promoter but no transgene (empty virus, or Ad.RR), or with the growth arrest medium used for suspending the virus (mock control). Multiplicities of infections (MOI, number of infectious virions/number of cells) were from 10 to 200. After six hours, the virus suspension or control medium was removed, and cells were washed twice with DMEM and fed with DMEM supplemented with 10% fetal bovine serum. Cells were counted every 24 hours, using a Coulter counter (Model Z1, Coulter Inc.).

DNA Analysis by Flow Cytometry

Human VSMC were plated at approximately $3.5 \times 10^5$ cells/60mm tissue culture dish for 7 day experiments and growth arrested for 60 hours as described above (cell count was approximately $4.5 \times 10^5$ on the day of infection). Cell density was at approximately $6 \times 10^5/60$ mm plate or $7.6 \times 10^5/100$ mm plate on the day of infection for 4-day experiments. Cells were then infected for six hours at the indicated MOI with Ad.E2F-1, Ad.RR (empty control virus), or mock control (growth arrest medium) as described above. Following removal of the virus, cells were washed twice with DMEM and growth-stimulated with DMEM supplemented with 10% FBS. At 24-hour intervals, cells were harvested for cell cycle and apoptosis analyses by DNA flow cytometry. Each sample was collected by pooling together detached cells in medium, attached cells, and all PBS washes before and after trypsinization. Samples were centrifuged for 10 min at 1800 rpm and then resuspended in 0.2 ml of PBS, followed by dropwise addition of 5 ml of ice-cold 85% ethanol while vortexing gently. Fixed cells were stored at −200° C. until all samples were collected. On the day of analysis, samples were centrifuged at 2500 rpm for 10 min and the ethanol was decanted. Cells were then washed once with PBS, centrifuged at 3000 rpm for 10 min. Each sample was resuspended in 200 or 400 μL of 100-μg/mL propidium iodide with 50 μg/ml RNase and incubated at 37° C. for 20 min. At least $4 \times 10^3$ cells were analyzed on the Coulter EPICS® Profile instrument (Miami, Fla.). Histograms were stored and files analyzed using Multicycle program from Phoenix Flow Systems (San Diego, Calif.).

E2F-1 immunohistochemistry

In order to assess whether E2F-1 was expressed in the VSMC at a time preceding the appearance of cell changes typical of apoptosis, VSMC infected with Ad.E2F-1, Ad.RR, and mock control were immunostained beginning at the completion of the six-hour infection. A mouse monoclonal antibody reactive with human E2F-1 was used as primary antibody (Santa Cruz Biotechnology, Santa Cruz, Calif.). Antibody binding was visualized with DAB, using a biotinylated secondary antibody and a streptavidin-biotin-horseradish peroxidase kit (Vector, Burlingham, Calif.). PBS with 0.1% Triton X-100 was used to suspend the antibodies and for all washing steps. VSMC were plated into chamber slides (Nalgen Nunc Intl., Naperville, Ill.) and serum-deprived for 60 hours and infected for six hours with Ad.E2F-1, Ad.RR, or mock control, as described above. After six hours, the virus was removed and cells were washed twice with DMEM then growth-stimulated in DMEM supplemented with 10% FBS. Cells were washed twice with phosphate-buffered saline (PBS), fixed for 10 min in three parts methanol and one part acetone at −20° C., and immunostained for E2F-1. Cells were counterstained with Alcian blue/methyl green in PBS, dehydrated in ethanol and coverslipped with Cytoseal 60 mounting medium (Stephens Scientific, Riverdale, N.J.).

Microscopy

Cell morphology was evaluated by combined epifluorescence and differential interference contrast (DIC) microscopy. Briefly, cells were passaged to glass slides and kept in serum-free medium for 60 hours prior to treatment. After incubation with Ad.E2F-1, Ad.RR or growth arrest medium alone, cells were stimulated by addition of DMEM with 10% FBS. Thirty hours after infection, the cells were incubated in the dark at 37° C. with 10 $\mu$g/ml of Hoechst 33342 and 4-(4-(dimethylamino)styryl)-N-methylpyridinium iodide (DASPMI) for staining of nuclear DNA and mitochondrial membranes, respectively. DNA staining and mitochondrial staining were, respectively, detected with a DAPI filter and a FITC filter set. All micrographs were digitally captured on a Zeiss Axioskop epifluorescence microscope using an Optronics (Goleta, Calif.) DEI-750 CCD color camera with Adobe Premiere software (Adobe Systems, Mountainview, Calif.), a TARGA 2000 video board (Truevision, Inc., Santa Clara, Calif.) and a PowerPC Macintosh 9500 (Apple Computer, Cupertino, Calif.). Images were edited with Adobe Photoshop software (Adobe Systems, Mountainview, Calif.).

Transduction of Human Vascular Smooth Muscle Cells (VSMC) with E2F-1

Figure 1A:
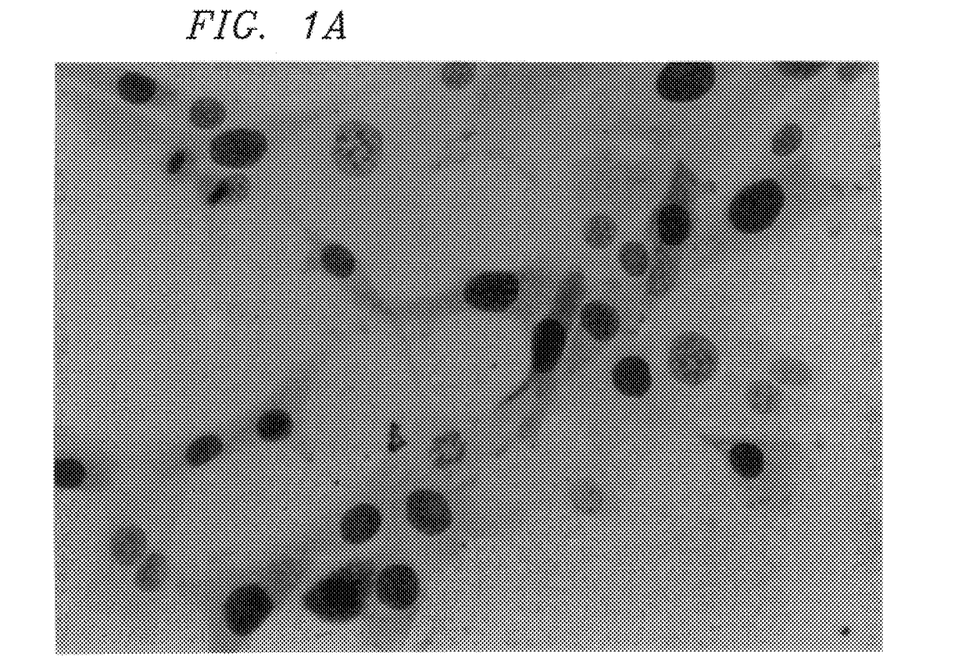
Figure 1B:
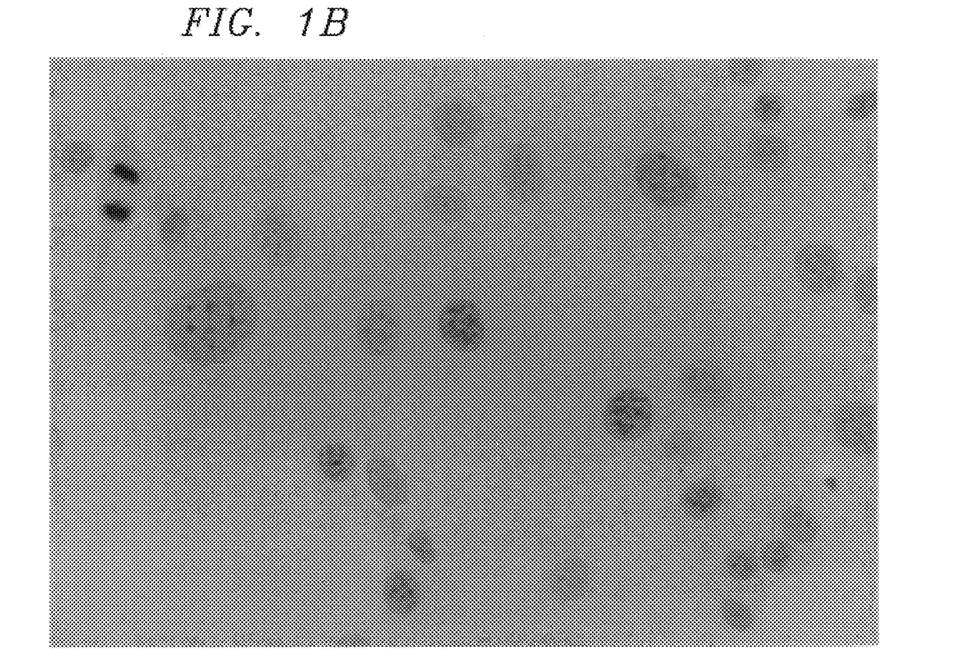

Growth-arrested human coronary VSMC were incubated at MOI 50 with Ad.E2F-1, Ad.RR, and mock control as described above and after various time periods processed for E2F-1 immunohistochemistry. Predominant nuclear E2F-1 immunostaining was present as early as 6 hours after start of infection as illustrated in FIG. 1A, or immediately after the removal of the Ad.E2F-1 in the transduced VSMC, whereas no staining was seen by 20 hours in control virus or mock treated cells (see FIG. 1B).

Overexpression of E2F-1 Forces Serum-Deprived Coronary VSMC to Enter S-Phase

Figure 2:
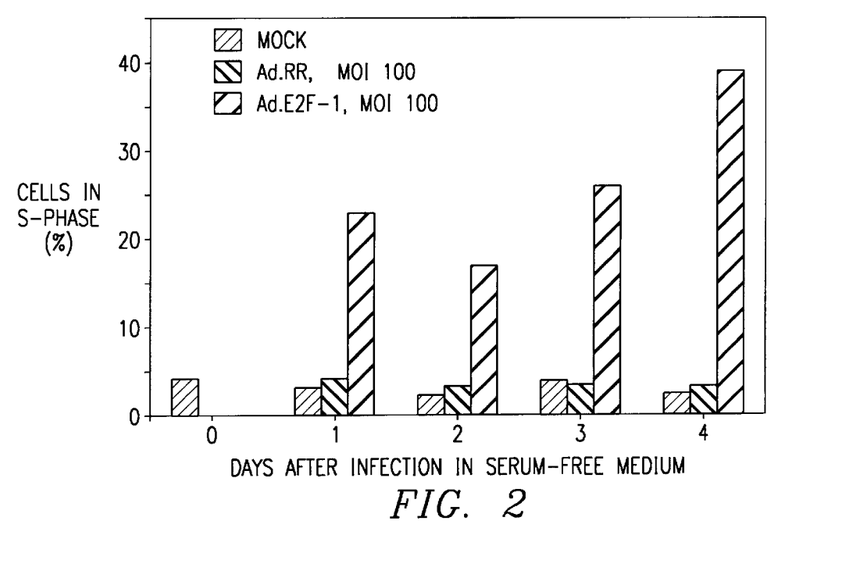
FIG. 2. Ad.E2F-1 promotes S-phase entry in growth arrested human VSMC. VSMC were serum deprived for 48 hours and infected with growth arrest medium alone (mock control), Ad.E2F-1 or Ad.RR at MOI of 100 for 6 hours. The cells were kept for an additional 4 days in serum-deprived medium. Cells were harvested every 24 hours and analyzed by DNA flow cytometry. Shown is the percentage of cells in S-phase over time.
Figure 3A:
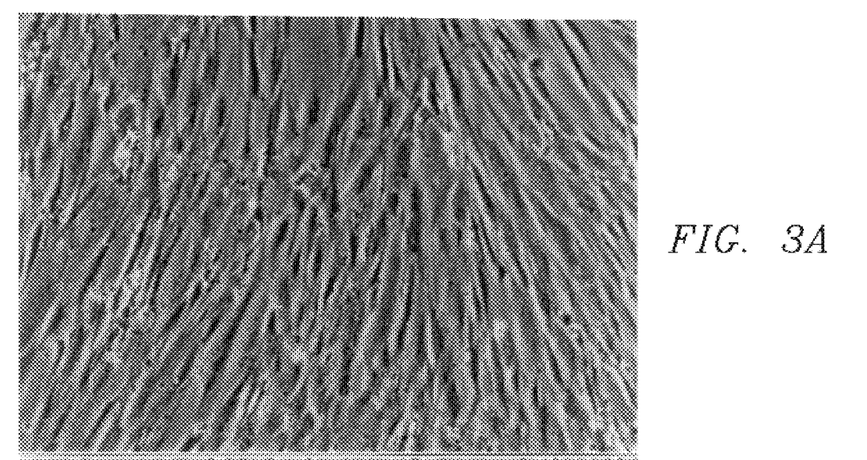
Figure 3B:
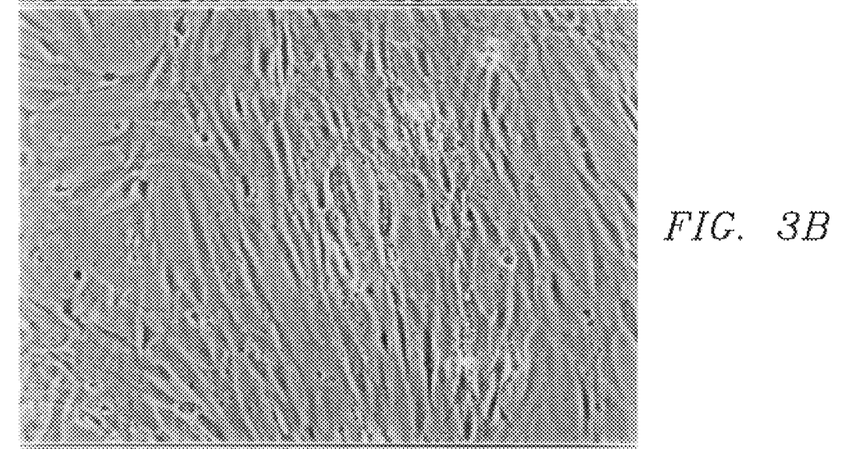
Figure 3C:
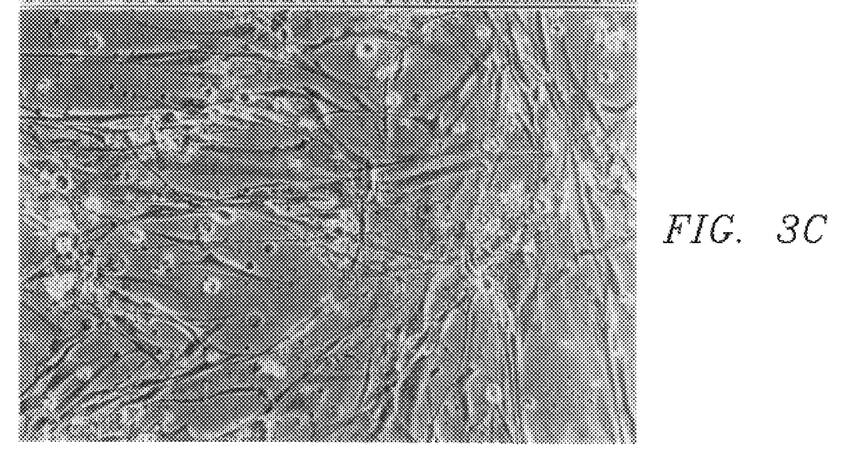

After demonstrating that E2F-1 was overexpressed in VSMC, DNA flow cytometry analysis of the cells was performed to verify that E2F-1 transfer had promoted S-phase entry of quiescent VSMC during growth arrest initiated by prolonged serum deprivation. Growth arrested cells were infected with Ad.RR, mock control and Ad.E2F-1 at MOI of 100, and kept in serum-free medium for an additional four days. Cells were harvested every 24 hours and processed for DNA flow cytometry. Despite prolonged serum deprivation, Ad.E2F-1 (but not Ad.RR or mock control) promoted S-phase entry in the quiescent VSMC, as shown by the flow cytometry results illustrated in FIG. 2. In contrast, the percentage of VSMC in S-phase remained consistently below 5% in the Ad.RR and mock-treated cells.

S-Phase Entry of E2F-1 Transduced Coronary VSMC is Associated With Induction of Apoptosis Within 24–36 hours after gene transfer of E2F-1 to VSMC, the induction of apoptosis was observed. Apoptotic changes, which were not observed after infection with the null adenoviral vector, Ad.RR, included membrane blebbing and loss of cytoplasmic membrane integrity, cell shrinkage and detachment, chromatin condensation, and loss of mitochondrial integrity ( see FIGS. 3A–3C and FIG. 4). Loss of mitochondrial membrane integrity was visualized with DASPMI, a mitochondrial membrane specific dye, as diffuse fluorescence alternating with areas of membrane condensation. Chromatin condensation and fragmentation were apparent as intensified fluorescence of nuclear fragments after staining with the intercalating DNA dye, Hoechst 33342.

Figure 4:
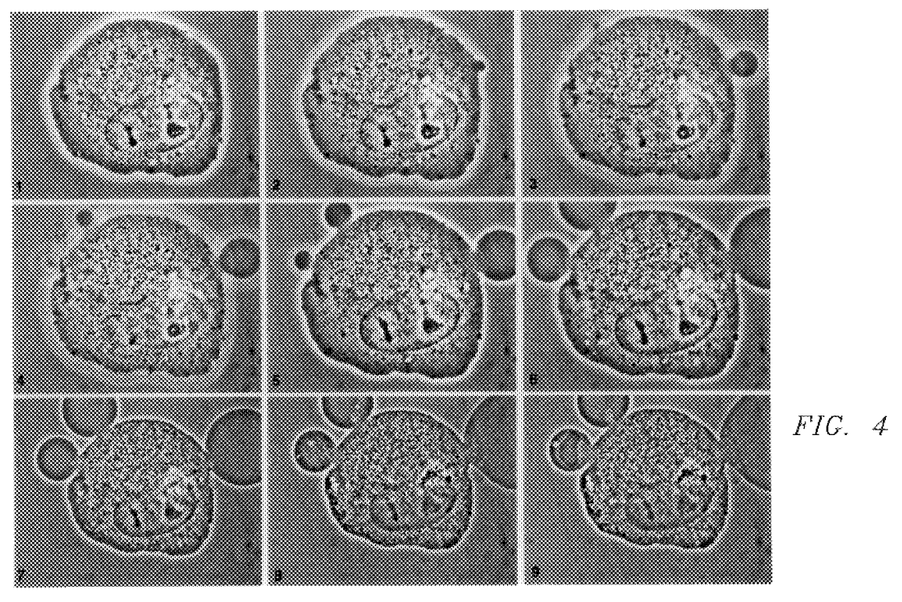
FIG. 4. Apoptosis in VSMC infected with Ad.E2F-1. Frames 1–9 show the changes observed in a single cell from the sample of coronary VSMC transduced with E2F-1 (MOI 100). Surface blebbing and loss of membrane integrity with extrusion of cellular contents were nearly complete within 2 hours after the first changes were observed (30–32 hours post-infection).

The development of apoptosis induced by E2F-1 expression occurred in a relatively short-time frame, as shown by video time lapse microscopy. FIG. 4 frames 1–9 show in phase-contrast the changes observed in a single cell from a sample of coronary VSMC transduced with E2F-1 (MOI 100). Surface blebbing and loss of membrane integrity with extrusion of cellular contents were nearly complete within 2 hours after the first changes were observed (30–32 hours post-infection).

Figure 5A:
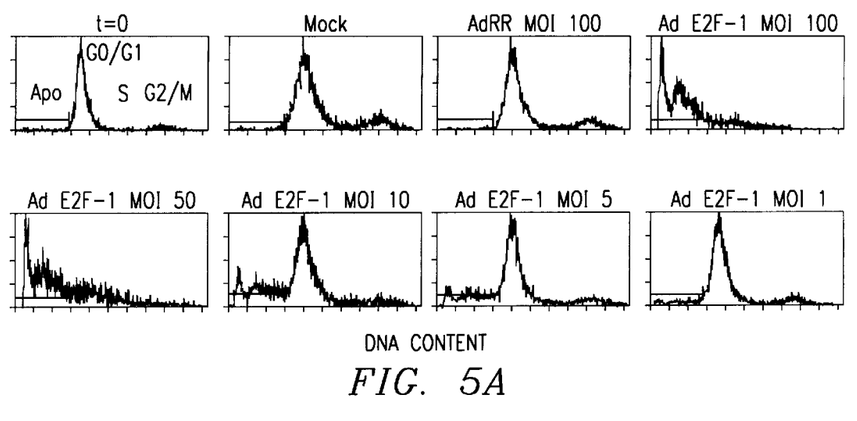
Figure 5B:
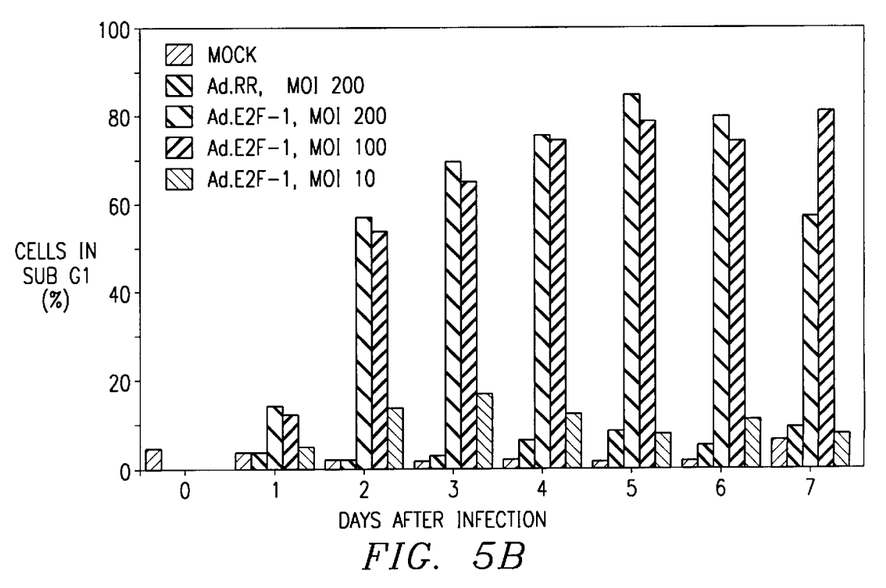

In order to evaluate time course and magnitude of apoptosis in coronary VSMC transduced with E2F-1, the cells were infected for six hours with Ad.E2F-1, Ad.RR, or mock control at MOI 10–200 followed by growth-stimulation in 10% FBS. The VSMC were harvested every 24 hours and subjected to DNA flow cytometry, which showed a dose-dependent induction of apoptosis by Ad.E2F-1, as reflected by the hypodiploid cell population in sub $G_1$ due to cleavage of DNA. Increases in the sub G0 fraction were observed with dosages of Ad.E2F-1 as low as MOI 5 (FIG. 5A). After the single application of Ad.E2F-1, induction of apoptosis involved a percentage of cells that appeared to increase over time. The sub $G_1$ fraction of VSMC peaked at 85% on day 5 with Ad.E2F-1 MOI 200 and at 17% on day 3 when a MOI of 10 was used, compared to respectively, 8% and 3%, with Ad.RR (FIG. 5B).

Growth suppression of VSMC in vitro after adenovirus-mediated gene transfer

Figure 6:
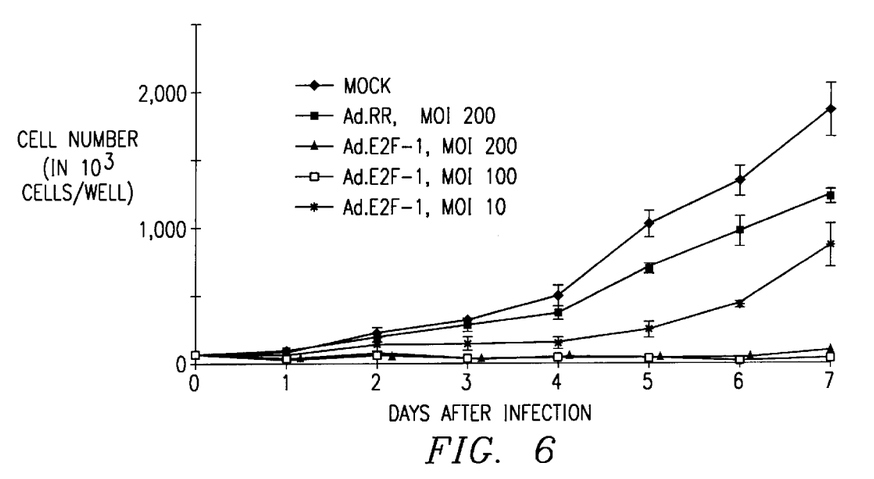
FIG. 6. Growth suppression of VSMC after adenovirus-mediated E2F-1 gene transfer. Growth curves were established for human coronary VSMC by daily counts of serum stimulated Ad.E2F-1, Ad.RR, and mock infected VSMC in triplicates.

After observing that E2F-1 transduced VSMC undergo apoptosis, the rate of cell death by apoptosis and the rate of cell proliferation were determined to ascertain if E2F-1 gene transfer would inhibit net growth of cultured VSMC. Growth curves were established for human coronary VSMC, infected with Ad.E2F-1, Ad.RR, or mock control. When cell growth was followed for seven days, it was observed that gene transfer of E2F-1 reduced VSMC growth after infection at MOI 10 and completely abolished growth after infection at MOI of 100 and 200 (FIG. 6).

An addition set of quiescent VSMC were infected for 6 hours at multiplicity of infection 100 with an adenovirus (Ad) encoding human E2F-1 or a control virus without foreign gene (Ad.RR), followed by serum stimulation for 6 days. E2F-1 expression, by immunohistochemistry, was observed within 6 hours after exposure to Ad.E2F-1. Cell counts were performed in conjunction with DNA flow cytometry to estimate apoptosis. By 24 hours, Ad.E2F-1 induced apoptotic features, including chromatin condensation, membrane blebbing, and cell detachment. After 2 days, 31.2±0.7% (mean±SD) of Ad.E2F-1 treated cells had undergone apoptosis, as indicated by the fraction of cells in sub G1 on DNA flow cytometry, and this percentage increased to 43.6±0.1% on day 4. In contrast, only 1.8±0.6% and 5.37±0.4% of Ad.RR infected VSMC were in sub G1 phase at 2 and 4 days, respectively. On day 6, the sub G1 fraction of Ad.E2F-1 infected VSMC was still higher than that of Ad.RR infected cells (20.0±5.4 versus 6.5±1.3, p<0.001). Of the surviving (cycling) VSMC, the percentage in S-phase, measured daily, ranged from 22.4±2.9 to 30.1±4.5 in Ad.E2F-1 treated cells, whereas the cells in S-phase decreased to 3.2±0.3% in the Ad.RR infected cells. Daily counts of serum-stimulated VSMC showed an increase in cell number (in 103 cells/well, N=3) from 265±1.9 (quiescence) to 3,585±395 six days after infection with Ad.RR, whereas Ad.E2F-1 treated cells increased to only 312±54 (p<0.001 compared to Ad.RR). Thus, gene transfer of E2F-1 to human VSMC promoted S-phase entry and apoptosis and thereby markedly suppressed serum-dependent growth.

These in vitro studies establish that gene transfer of E2F-1 induces death of VSMC by inducing apoptosis and thereby reduces the proliferating VSMC mass. Induction of cell death will irreversibly eliminate the VSMC as a source of paracrine and autocrine growth factors and extracellular matrix, which significantly contribute to the pathogenesis of the restenotic lesion. In addition, any potential for intimal migration of VSMC is abrogated after the VSMC dies.

Influence of Ad.E2F-1 in an Atherosclerotic Animal Model

Under approved protocols, male New-Zealand rabbits (12 months of age) were fed for 28 days a 0.75% cholesterol-enriched chow and exhibited severe hypercholesterolemia. After this period, the rabbits were anesthetized, underwent transfemoral carotid balloon angioplasty, followed by a 30-min. local dwell-delivery of Ad.E2F-1 virus or control (Ad.RR) virus to the site of carotid balloon injury. Ad.RR was given to the balloon injured rabbits at $1\times10^{10}$ pfu/ml and Ad.E2F-1 was administered at $1\times10^{10}$, $1\times10^{9}$, and $3\times10^{8}$ pfu/ml. After balloon angioplasty and virus delivery, the animals were allowed to recover and were kept for 28 days after surgery on the cholesterol-enriched diet. Twenty-eight days after surgery, the animals were sacrificed, and were pressure-perfused with neutral-buffered formaldehyde using standard techniques. This model closely corresponds to the atherosclerosis model of Pollman and associates (Pollman et al., 1998). The injured and uninjured carotid arteries were harvested. Paraffin-embedded arterial segment sections were prepared every 2-mm, and were stained with the Verhoeft/Van Giessen (elastic) stain, followed by quantitative histomorphometry, using standard equipment. The administration of Ad.E2F-1 at $3\times10^{9}$ pfu/ml significantly reduced atherosclerotic lesion formation compared to control virus. In addition, the lesions in the E2F-1 ($3\times10^{9}$ pfu/ml) treated animals appeared to be less lipid-rich. Yet plasma cholesterol in Ad.RR ($1\times10^{10}$ pfu/ml) treated rabbits was $820\pm116$ mg/dl and $988\pm324$ mg/dl in Ad.E2F-1 ($3\times10^{9}$ pfu/ml) treated animals.

These experiments were repeated in male and female New-Zealand rabbits as described below, where Ad.RR and Ad.E2F-1 were administered at the same dosage of $3\times10^{9}$ pfu/ml. Expression of adenovirally mediated foreign expression was demonstrated in balloon-injured carotid arteries by immunohistochemistry with antibodies recognizing E2F-1 (clone KH95, Santa Cruz Biotechnology, Inc.). Anesthesia was induced in rabbits of either sex with xylazine and ketamine and maintained with isofluorane in oxygen.

A left femoral cut-down was performed. After insertion of a 5-F sheet into the left femoral artery 150 units of unfractionated heparin, 150 units/kg, were given intravenously. Then, a 5-F balloon angioplasty catheter with a 20×2.5 mm balloon was introduced into the sheath and advanced over a 0.014 inch guide wire to the right common carotid artery. A carotid cut-down was performed and the position of the balloon was adjusted so that its center was at the level of the branching point of the common carotid artery. This internal carotid artery was tied off and marked the center of the balloon-injured segment. The balloon was inflated 5 times for 30 sec to 8 atm, with a 60 sec interval between inflations.

The catheter, with the balloon deflated under suction, was withdrawn to the caudal (proximal) end of the injured carotid segment, which was ligated temporarily with umbilical tape in a fashion that left included in the isolated vascular segment the proximal catheter tip. Then, the guide wire was removed from the animal. Through the opening of the wire lumen at the catheter tip 10 ml of physiological saline solution was introduced into the injured carotid segment to remove the blood in the injured segment. Then, the distal end of the injured carotid segment was temporarily ligated with a second umbilical tape. All remaining saline was removed from the isolated carotid segment and purified recombinant adenoviral vectors at $3\times10^{9}$ pfu/ml were introduced through the wire lumen of the angioplasty balloon catheter into the temporarily isolated lumen of injured carotid artery in an amount sufficient to barely distend the isolated segment. Ad.RR, the control vector, and Ad.E2F-1 were administered in the same manner. The suspension containing the adenoviral vectors were left in situ for 30 min, followed by their removal through the catheter. The umbilical tape was released and the catheter was withdrawn from the animal and the umbilical tape was removed from the injured carotid artery to allow return of blood flow into the carotid artery. The femoral and carotid cut-down was repaired and the rabbits were allowed to recover.

Dalteparin, 60 units/kg (Fragmin, Pharmacia & Upjohn, Kalamazoo, Michigan) was given every 12 hours for 2 doses, beginning 1 hour after angioplasty. Following removal of the catheter from the animal, the animals were returned to their cages and sacrificed 4 and 28 days after surgery, respectively, to confirm local expression of E2F-1 and to evaluate the site of injury for neointima formation.

Four days after surgery, some animals were sacrificed after pressure perfusion-fixation with 10% buffered formaldehyde. The balloon-injured carotid arteries were harvested and arterial rings were processed and embedded in paraffin using standard procedures. Following preparation of 5 $\mu$m sections, these were post-fixed for 15 minutes in 4% formaldehyde. After exposure for 10 minutes to 3% $H_2O_2$ in methanol, the sections were blocked for 20 minutes in 2% horse serum in PBS and exposed for 1 hour at room temperature to a monoclonal antibody to human E2F-1 (clone KH95, Santa Cruz Biotechnology, Inc.) or cytomegalovirus (DAKO, Carpinteria, California) as negative control.

Sections were exposed for 30 min to a biotinylated horse antimouse antibody (VectorLabs) and incubated for 30 minutes in streptavidin-biotin-horse radish peroxidase (VectorLabs). Antibody binding was visualized by exposure to DAB (Vector Labs) and sections were counterstained in 1% Alcian blue and 2% methyl green (VectorLabs) or hematoxylin & eosin, using routine procedures. PBS was used for washes. These methods confirmed E2F-1 expression in rabbit carotid arteries treated with Ad-E2F-1 for 30 min.

Twenty-eight days after surgery, the rabbits were sedated and anesthetized with xylazine and ketamine. A carotid cut-down was performed on the side previously injured. Then, the animal was pressure perfusion-fixed with 10%-buffered formaldehyde and the injured carotid segment and a short segment of the contralateral carotid artery were harvested into 10%-buffered formaldehyde.

The arteries were cut in about 2 mm rings and, using routine histology procedures, embedded in paraffin. Several arterial rings were placed next to each other in each mold, facilitating later preparation and evaluation on sections from (2-mm) adjacent sampling sites of the same carotid segment. About 5–9 arterial rings were obtained from each injured carotid segment, allowing sampling of the same number of histomorphometric measurements per carotid segment. Sections used for histomorphometric analysis were stained with a Verhoeft-Van Gieson elastic stain and magnified images were captured using a Axiophot microscope (Zeiss, West Germany) and Lumina videocamera (Lumina, Lefs Systems, Co.). Images were processed with software from Optima Imaging Analysis Systems 4.1. Measurements were performed by a technician unaware of the treatment the rabbits had received.

Figure 7:
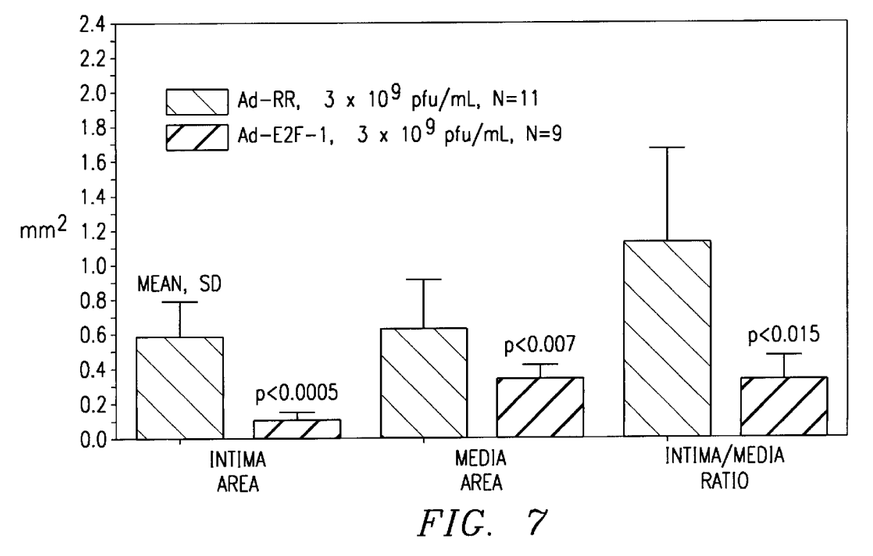
FIG. 7. The influence of Ad.E2F-1 compared to control virus (Ad.RR) on the intima area, the media area, and the intima/media ratio 28 days after balloon injury in cholesterol-fed hypercholesterolemic New Zealand white rabbits.
Figure 8:
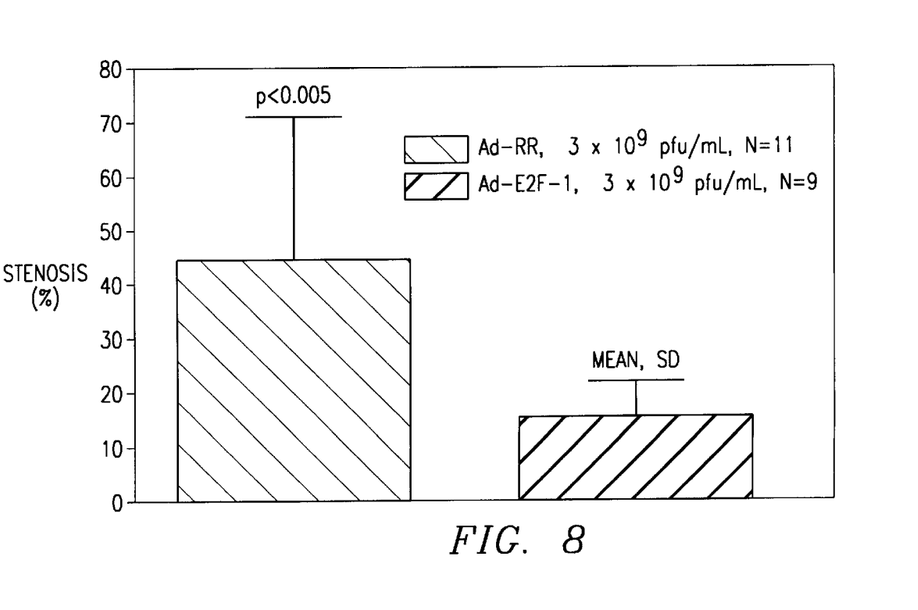
FIG. 8 The influence of Ad.E2F-1 compared to control virus (Ad.RR) on the percentage of stenosed carotid arteries 28 days after balloon injury in cholesterol-fed hypercholesterolemic New Zealand white rabbits.

The results of this histomorphometric analysis is shown in FIGS. 7 and 8 and indicate the gene transfer of E2F-1 at $3 \times 10^9$ pfu/ml markedly suppresses neointima/arteriosclerosis lesion formation in the Ad.E2F-1 treated rabbit arteries.

The success of the E2F-1 gene transfer to prevent primary atherosclerotic lesions in the rabbit model illustrates that gene transfer of E2F-1 can prevent atheromatous and fibroproliferative lesion formation in vivo despite severe elevation of cholesterol levels. Thus, E2F-1 gene transfer to arteries and vein grafts can be used to prevent or significantly reduce atherogenesis and fibroproliferative disorders in arteries, veins, grafts, arteriovenous fistulas and stent grafts.

While the preferred embodiment of the invention has been shown and described, modifications thereof can be made by one skilled in the art without departure from the spirit and teachings of the invention. The embodiment described herein is exemplary only and is not limiting. Many variations and modifications of the invention disclosed herein are possible and are within the scope of the invention. Accordingly, the scope of protection is not limited by the description set out above, but is only limited by the claims which follow, that scope including all equivalent subject matter of the claims.

REFERENCES

The patents and technical publications referred to herein are incorporated by reference to the extent that they provide any necessary methods and materials not specifically set forth herein.

Agah, R., Kirshenbaum, L. A., Abdellatif, M., Truong, L. D., Chakraborty, S., Michael, L. H., Schneider, M. D. Adenoviral delivery of E2F-1 directs cell cycle reentry and p53-independent apoptosis in postmitotic adult myocardium in vivo. 1997. *J Clin Invest;* Dec 1 100(11):2722–2728

Chang, M. W., Barr, E., Seltzer, J., Jiang, Y-Q., Nabel, G. J., Nabel, E. G., Pannacek, M. S., Leiden, J. M. Cytostatic gene therapy for vascular proliferative disorders with a constitutively active form of the retinoblastoma gene product. 1995. *Science;* 267(5197):518–522.

Clowes, A. W., Reidy, M. A., Clowes, M. M. Kinetics of cellular proliferation after arterial injury. I. Smooth muscle growth in the absence of endothelium. 1983. *Lab Invest;* 49(3):327–333.

DeGregori, J., Leone, G., Alexander, M., Jakoi, L., Nevins, J. R. Distinct roles for E2F proteins in cell growth control and apoptosis. 1997. *Proc Natl Acad Sci* USA; Jul 8 94 (14): 7245–7250.

Fueyo, J., Gomez-Manzano, C., Yung, W. K. A., Liu, T. J., Alemany, R., McDonnell, T. J., Shi, X., Rao, J. S., Levin, V. A., Kyritsis, A. P. Overexpression of E2F-1 in glioma triggers apoptosis and suppresses tumor growth in vitro and in vivo. 1998. *Nature Medicine;* Jun 4 (6):685–690.

Gomez-Foix, A. M., Coats, W. S., Baque, S., Alam, T., Gerard, R. D., Newgard, C. B. Adenovirus-mediated transfer of the muscle glycogen phosphorylase gene into hepatocytes confers altered regulation of glycogen metabolism. 1992. *J Biol Chem* Dec 12 267(35):25129–25134.

Gordon, D., Reidy, M. A., Benditt, E. P., Schwartz, S. M. Cell proliferation in human coronary arteries. 1990. *Proc Natl Acad Sci* USA Jun 87 (12):4600–4604.

Griffith, T. S., Brunner, T., Fletcher, S. M., Green, D. R., and Ferguson, T. A. Fas ligand-induced apoptosis as a mechanism of immune privilege. 1995. *Science,* Nov 17 270(5239): 1189–1192.

Helin, K., Lees, J. A., Vidal, M., Dyson, N., Harlow, E., and Fattaey. A. A cDNA encoding a pRB-binding protein with properties of the transcription factor E2F. 1992. *Cell* 70:337–350.

Hunt, K. K., Deng, J., Liu, T. J., Wilson-Heiner, M., Swisher, S. G., Clayman, G., Hung, M. C. Adenovirus mediated overexpression of the transcription factor E2F-1 induces apoptosis in human breast and ovarian Carcinoma cell lines and does not require p53. 1997. *Cancer Res Nov* 1 57(21):4722–4726.

Johnson, D. G., Cress, W. D., Jakoi, L., and Nevins, J. R. Oncogenic capacity of the E2F-1 Gene. 1994. *Proc. Natl. Acad. Sci.* USA 91:12823–12827.

Kowalik, T. F., Degregori, J., Schwarz, J. K., and Nevins, J. R. E2F1 overexpression in quiescent fibroblasts leads to induction of cellular DNA synthesis and apoptosis. 1995. *J Virol.* 69:2491–2500.

Li, Y., Slansky, J. E., Myers, D. J., Drinkwater, N. R., Kaelin, W. G., Farnham, P. J. Cloning, chromosomal location, and characterization of mouse E2F1. 1994. *Mol Cell Biol* Mar 14(3):1861–1869.

McGrory, W. J., Bautista, D. S., Graham, F. A simple technique for the rescue of early region I mutations into human adenovirus type 5. 1988. Virology Apr 163(2) :614–167.

Neuman, E., Sellers, W. R., McNeil, J. A., Lawrence, J. B., and Kaelin, Jr., W. G. Structure and partial genomic sequence of the human E2F1 gene. 1996. *Gene Sep* 16; 173(2):163–169.

Nevins, J. R. E2F: a link between the Rb tumor suppressor protein and viral oncoproteins. 1992. *Science* 258:424429.

O'Brien, E. R., Alpers, C. E., Stewart, D. K., Ferguson, M., Tran, N., Gordon, D., Benditt, E. P., Hinohara, T., Simpson, J. B., Schwartz, S. M. Proliferation in primary and restenotic coronary atherectomy tissue. Implications for antiproliferative therapy. 1993. *Circ Res; Aug* 7 73(2) :223–231.

Ohno, T., Gordon, D., San, H., Pompili, V. J., Imperiale, M. J., Nabel, G. J., Nabel, E. G. Gene therapy for vascular smooth muscle cell proliferation after arterial injury. 1994. *Science* Aug 5 265(5173):781–784.

Pollman, M. J., Hall, J. L., Mann, M. J., Zhang, L., Gibbons, G. H. Inhibition of neointimal cell bc1-x expression induces apoptosis and regression of vascular disease. 1998. *Nature Medicine;* Feb 4(2):222–227.

Qin, X. Q., Livingston, D. M., Ewen, M., Sellers, W. R., Arany, Z., and Kaelin, W. G. The transcription factor E2F-1 is a downstream target of RB action. 1995. *Mol. Cell BioL* 15: 742–755.

Qin, X. Q., Livingston, D. M., Kaelin, W. G., Jr., and Adams, P. D. Deregulated transcription factor E2F-1 expression leads to S phase entry and p53-mediated apoptosis. 1994. *Proc. Natl. Acad. Sci.* USA 91: 10918–10922.

Sata, M., Perlman, H., Muruves, D. A., Silver, M., Ikebe, M., Libermann, T. A., Oettgen, P., Walsh, K. Fas ligand gene transfer to the vessel wall inhibits neointima formation and overrides the adenovirus-mediated T-cell response. 1998. *Proc Nati Acad Sci* USA; Feb 3 95(3):1213–1217.

Schwartz, R. S., Edwards, W. D., Huber, K. C., Antoniades, L. C., Bailey, K. R., Camrud, A. R., Jorgenson, M. A., Holmes, D. R., Jr., Coronary restenosis: prospects for solutions and new perspectives from a porcine model. 1993. *Mayo Clin Proc;* Jan 68(1):54–62.

Schwartz, S. M., deBlois, D., O'Brien, E. R. The intima: soil for atherosclerosis and restenosis. 1995. *Circ Res;* Sep 77(3):445–4465.

Schwartz, S. M., Reidy, M. A., deBlois, D. Factors important in arterial narrowing. 1996. *J Hypertension* Dec. 14 (5):S71–S81.

Shan, B. and Lee, W. H. Deregulated expression of E2F-1 induces S phase entry and leads to apoptosis. 1994. *Mol. Cell Biol.* 14:8166–8173.

Shan, B., Durfee, T., and Lee, W. H. Disruption of RB/E2F-1 interaction by single point mutations in E2F-1 enhances S phase entry and apoptosis. 1996. Proc. Natl. Acad. Sci. USA 93:679–684.

Singh, P., Wong, . H., and Hong, W. Overexpression of E2F-1 in rat embryo fibroblasts leads to neoplastic transformation. 1994. *EMBO J.* 13:3329–3338.

Xu, G., Livingston, D. M., and Krek, W. Multiple members of the E2F transcription factor family and the products of oncogenes. 1995. *Proc. Natl. Acad Sci.* USA 92:1357–1361.

Yonemitsu, Y., Kaneda, Y., Hata, Y., Nakashima, Y., Sueishi, K. Wild-type p53 gene transfer: a novel therapeutic strategy for neointima hyperplasia after arterial injury. 1997. *Ann NY Acad Sci* Apr. 15 811:395–400.

We claim:

1. A method of reducing or preventing vascular smooth muscle cell accumulation in vascular tissue comprising transferring directly to vascular smooth muscle cells in the vascular tissue a transgene comprising a DNA sequence encoding the E2F-1 protein operably linked to a promoter, whereby the expression of said transgene results in an increased amount of E2F-1 protein in said vascular smooth muscle cells in an amount effective to induce vascular smooth muscle cell apoptosis, wherein the apoptosis of the vascular smooth muscle cells results in the reduction or prevention of vascular smooth muscle cell accumulation in said tissue.

2. The method of claim 1 wherein the vascular tissue is an arteriovenous fistula used for dialysis access.

3. The method of claim 1 wherein the vascular tissue is a venous graft.

4. The method of claim 1 wherein the vascular tissue is a saphenous coronary by-pass graft.

5. The method of claim 1 wherein the vascular tissue is a peripheral arterial by-pass graft.

6. The method of claim 1 wherein the vascular tissue is vascular tissue after a percutaneous revascularization intervention.

7. The method of claim 1 wherein the vascular tissue is vascular tissue after balloon angioplasty.

8. The method of claim 1 wherein the vascular tissue has had a vascular stent administered.

9. A method of reducing or preventing restinosis in vascular tissue comprising transferring directly to vascular smooth muscle cells in the vascular tissue comprising a transgene a DNA sequence encoding the E2F-1 protein operably linked to a promoter, whereby the expression of said transgene results in an increased amount of E2F-1 protein in said cells in an amount effective to induce vascular smooth muscle cell apoptosis, wherein the apoptosis of the vascular smooth muscle cells results in the reduction or prevention of restinosis in said tissue.

10. The method of claim 9 wherein the vascular tissue is a venous graft.

11. The method of claim 9 wherein the vascular tissue is a saphenous coronary by-pass graft.

12. The method of claim 9 wherein the vascular tissue is a peripheral arterial by-pass graft.

13. The method of claim 9 wherein the vascular tissue is vascular tissue after a percutaneous revascularization intervention.

14. The method of claim 9 wherein the vascular tissue is vascular tissue after balloon angioplasty.

15. The method of claim 9 wherein the vascular tissue has had a vascular stent ad ministered.

16. A method of reducing or preventing stenosis in vascular tissue wherein said tissue is an arteriovenous fistula used for dialysis comprising transferring directly to vascular smooth muscle cells in the vascular tissue a transgene comprising a DNA sequence encoding the E2F-1 protein operably linked to a promoter, whereby the expression of said transgene results in an increased amount of E2F-1 protein in said cells in an amount effective to induce vascular smooth muscle cell apoptosis, wherein the apoptosis of the vascular smooth muscle cells results in the reduction or prevention of stenosis in said tissue.

17. A method of reducing or preventing formation of an atherosclerotic lesion in vascular tissue comprising transferring directly to vascular smooth muscle cells in the vascular tissue a transgene comprising a DNA sequence encoding the E2F-1 protein operably linked to a promoter, whereby the expression of said transgene results in an increased amount of E2F-1 protein in said cells in an amount effective to induce vascular smooth muscle cell apoptosis, wherein the apoptosis of the vascular smooth muscle cells results in the reduction or prevention of an atherosclerotic lesion in said tissue.

18. The method of claim 17 wherein said transferring comprises transferring to a site chosen from the group consisting of an artery, vein graft, arteriovenous fistula, stent graft, or portion thereof 19. A method of reducing or preventing vascular smooth muscle cell accumulation at a site in vascular tissue comprising transferring to the vascular smooth muscle cells in the vascular tissue an adenovirus vector comprising a human cytomegalovirus promoter, a E2F-1 cDNA, and a bovine hormone polyadenylation signal, whereby the expression of said transgene results in an increased amount of E2F-1 protein in said cells in an amount effective to induce vascular smooth muscle cell apoptosis, wherein the apoptosis of the vascular smooth muscle cells results in the reduction or prevention of vascular smooth muscle cell accumulation in said tissue.

20. The method of claim 19 wherein said site is a venous graft, or portion thereof.

21. The method of claim 19 wherein said site is a arteriovenous fistula, or portion thereof.

22. The method of claim 19 wherein said site is a stent graft, or portion thereof.

23. A method for transforming a population of vascular smooth muscle cells, said cells transformed such that E2F-1 expression is increased in said cells and wherein and increased expression of E2F-1 reduces the accumulation of smooth muscle cells at a site of vascular injury in a artery, vein graft, arteriovenous fistula, sten graft, or portion thereof.

* * * * *